United States Patent [19]

Oksman et al.

[11] Patent Number: 4,578,358

[45] Date of Patent: Mar. 25, 1986

[54] COLLECTION OF SPECIMENS AND DETECTION OF OCCULT BLOOD THEREIN

[75] Inventors: Norman H. Oksman, Mount Vernon, N.Y.; Joseph M. Talmage, Landing, N.J.; Henry J. Wells, Beaumont, Tex.

[73] Assignee: Warner-Lambert Company, Morris Plains, N.J.

[21] Appl. No.: 491,007

[22] Filed: May 3, 1983

[51] Int. Cl.$^4$ .................. G01N 1/02; G01N 33/52; G01N 33/72

[52] U.S. Cl. .................. 436/66; 128/638; 128/759; 422/56; 435/28

[58] Field of Search .............. 128/749, 759, 638; 422/55, 56, 57, 58; 436/66, 169, 170; 435/28; 428/284; 604/361

[56] References Cited

U.S. PATENT DOCUMENTS

| | | | |
|---|---|---|---|
| 3,718,431 | 2/1973 | Wild | 128/749 X |
| 4,082,886 | 4/1978 | Butterworth et al. | 428/284 |
| 4,175,923 | 11/1979 | Friend | 436/66 |
| 4,259,964 | 4/1981 | Levine | 128/759 X |
| 4,273,741 | 6/1981 | Levine | 422/56 |
| 4,333,734 | 6/1982 | Fleisher | 436/66 |
| 4,365,970 | 12/1982 | Lawrence et al. | 436/66 |
| 4,420,353 | 12/1983 | Levine | 422/56 X |

FOREIGN PATENT DOCUMENTS 0901754 6/1972 Canada .
1018563 1/1966 United Kingdom .............. 436/169

OTHER PUBLICATIONS

Rider et al., Journal of the American Medical Association, vol. 156, pp. 31-33 (9/4/54).

Primary Examiner—Barry S. Richman
Assistant Examiner—Robert J. Hill, Jr.
Attorney, Agent, or Firm—Gary M. Nath

[57] ABSTRACT

A test for the presence of occult blood in fecal matter or other bodily substance employs an indicator wipe 2. The indicator wipe 2 has an occult-blood detection-test surface 10 for collecting a specimen and includes a peroxidase-activity indicator reagent dispersed on or located proximate to the specimen collection region. The test involves contacting the specimen-collection region to the bodily substance to obtain a specimen, then applying an oxidizing-agent developing fluid to the specimen and observing any color change to determine if the specimen contains occult blood, and finally disposing of the indicator wipe by placing it in a toilet bowl and flushing it away.

10 Claims, 2 Drawing Figures

COLLECTION OF SPECIMENS AND DETECTION OF OCCULT BLOOD THEREIN

DESCRIPTION

TECHNICAL FIELD

The present invention relates to a process for collecting specimens of fecal matter or other bodily substance and testing the specimens for the presence of occult blood.

BACKGROUND ART

The presence of blood in feces can signal the existance of a tumor, ulcer, or other medical disorder along the digestive tract. In early stages of development, a tumor or ulcer on the digestive tract may bleed to such a slight extent that the blood, while present in the feces, is not visible. Nonetheless, in such cases, the blood, termed "hidden" or "occult" blood, can usually be detected with one of a number of indicator reagents which change color in the presence of the hemoglobin in blood.

One of the most widely used occult-blood indicator reagents is derived from an extract from the wood of certain species of trees of the Guaiacum genus native to the American tropics. The extract, termed guaiac, turns from essentially colorless to blue in the presence of hemoglobin and an oxidizing agent such as hydrogen peroxide. More specifically, the guaiac reagent is sensitive to what is termed "peroxidase activity" which results from the combination of an oxidizing agent with hemoglobin or certain chemically similar compounds.

Testing feces for the presence of occult blood with an occult-blood indicator reagent is a valuable medical diagnostic tool, since such testing can often detect tumors in the digestive tract at an early stage of their development, typically before the tumors manifest other symptoms and at a stage when they can be treated most successfully.

A procedure widely used by physicians and medical laboratories for testing for occult blood in fecal matter makes use of a test slide of the type disclosed in U.S. Pat. No. 4,365,970 to Lawrence and Townsley. The test slide of the Lawrence and Townsley patent includes a sheet of guaiac-impregnated indicator paper enclosed in a cardboard envelope. A front panel of the envelope has openings in it for smearing samples of fecal matter on a first side of the indicator paper. A rear panel of the envelope has an opening for applying a hydrogen peroxide developing solution to a second side of the indicator paper. A blue stain on the indicator paper signifies the presence of occult blood in the sample of fecal matter on the opposite side. Since the blue stain appears on the side of the indicator paper opposite to the samples of fecal matter, the developing solution necessarily soaks through the paper in the test procedure. The indicator sheet of the test slide of the Lawrence and Townsley patent has a control area designated on its second side which includes a positive monitor and a negative monitor. Hemin, a hemoglobin-derived compound, is printed on the positive monitor, but not on the negative monitor. Application of the developing solution to the control area causes the indicator paper to turn blue at the positive monitor and remain colorless at the negative monitor if the test reagents are properly active and if the test slide has not been contaminated with a compound which yields a false indication of the presence of hemoglobin.

Although the test slide of the Lawrence and Townsley patent is generally satisfactory for use in a doctor's office or a hospital, it has significant disadvantages for home use. An applicator stick must be used to collect each sample of fecal matter from a toilet bowl and to smear the sample on the test slide. The person using the test slide thus has the problem of disposing of the applicator sticks and, after applying the developing solution to the slide, disposing of the test slide itself. Neither the applicator sticks nor the test slide can be flushed down the toilet. Even if the test slide is forwarded to a doctor's office or medical laboratory for analysis, the problem of disposing of the soiled applicator sticks remains for the user.

U.S. Pat. No. 4,175,923 to Friend discloses a test for the presence of occult blood in fecal matter which is intended to be carried out at home. The test makes use of an indicator paper prepared by impregnating a sheet of absorbent paper with guaiac reagent. A portion of the indicator paper is also impregnated with blood. The test of the Friend patent involves applying a developing solution to a sheet of the indicator paper and then tossing the sheet into a toilet bowl to contact the paper with the water in the bowl. The developing solution causes the portion of the indicator paper impregnated with blood to turn blue if the guaiac reagent and developing solution are properly active. If stools in the toilet bowl contain occult blood, blood will disperse in the water in the bowl. Blood in the water in the toilet bowl will in turn cause the remainder of the indicator paper to turn blue. After allowing time for the color of the indicator paper to change, the paper can be flushed down the toilet with the stools.

Although the occult-blood detection test of the Friend patent is satisfactory in principle, it is limited in a number of respects. Ordinarily, for occult blood in fecal matter to be detected by the test, the blood must disperse in the water of the toilet bowl. Such dispersal necessarily dilutes the blood and thus reduces the sensitivity of the test. In addition, the test results may be suspect as a consequence of the presence of contaminants in the toilet bowl.

DISCLOSURE OF THE INVENTION

We have invented a process for collecting a specimen of fecal matter or other bodily substance and detecting the presence of occult blood in the specimen which is suitable for carrying out at home and which avoids problems of the prior art noted above.

The invention makes use of an occult-blood indicator wipe which has a specimen-collection region defined on it. The indicator wipe includes a peroxidase-activity indicator reagent such as guaiac reagent dispersed on or located proximate to the specimen-collection region of the detection-test surface. The indicator wipe is made of a pliable material which has a sufficiently low wet strength to permit the wipe to be disposed of in a toilet.

Broadly, the process of the invention includes contacting the specimen-collection region of the occult-blood indicator wipe with a bodily substance such as fecal matter to collect a specimen of the substance.

The process further includes applying an oxidizing-agent developing fluid to the specimen collected on the indicator wipe and observing any change of color to determine if the specimen includes occult blood.

Finally, the process of the invention includes placing the indicator wipe in a toilet bowl and flushing the toilet to dispose of the wipe and the specimen of bodily substance.

A preferred indicator wipe for the invention has a hand-contact surface for manipulating the wipe and an occult-blood detection test surface on which is defined the specimen-collection region. The preferred indicator wipe is of a size and shape to be readily manipulated by hand. A wide range of sizes and shapes are usable. A preferred indicator wipe is in the form of a generally rectangular pad from about 80 mm to about 150 mm wide and from about 100 mm to about 200 mm long. Dimensions of roughly 100 mm wide by roughly 150 mm long are particularly preferred. Alternatively, the indicator wipe could be circular or oval in shape. The indicator wipe could also be fabricated as a mitt to be worn over the hand. It will be recognized that the indicator wipe for use in the process of the invention could be fabricated in other forms and sizes.

The indicator wipe preferably has a sufficiently high resistance to seepage by the developing fluid from the detection-test surface to the hand-contact surface to permit the hand-contact surface to remain dry for the duration of an occult-blood detection test.

A preferred indicator wipe is a generally rectangular pad formed from a number of sheets of absorbent, porous, soft, low-wet-strength paper of the type used as toilet tissue. The sheets are arranged one on top of the other. For example, a pad composed of nine plies of tissue paper is particularily preferred. However, either a greater or lesser number of plies may be advantageous in certain applications, depending, for example, on the weight and stiffness of the individual plies of tissue paper.

In a preferred indicator wipe formed from plies of low-wet-strength tissue paper, the plies are preferably joined together around their periphery. The plies may be joined by crimping. Crimping the plies together around the periphery of the pad permits the plies to separate from one another readily when the indicator wipe is soaked with water. Consequently, the indicator wipe may be safely disposed of in a toilet. Furthermore, a pad formed from plies of tissue paper crimped together is economical to manufacture. Alternatively, the plies of tissue paper may be joined with an adhesive, preferably applied around the periphery of the pad. The adhesive is preferably water soluble or otherwise water degradable to permit the indicator wipe to be disposed of readily in a toilet.

The indicator wipe for use in the invention is preferably biodegradable.

A preferred peroxidase-activity indicator reagent for the invention is guaiac reagent. As used herein, the term guaiac reagent includes resin guaiac; individual components of resin guaiac such as alpha-guaiaconic acid, beta-guaiaconic acid, guaiacic acid and related compounds, guaiaretic acid and guaiacin; and mixtures thereof. Other peroxidase-activity indicator reagents which are suitable in certain applications include aniline and its derivatives, o-tolidine, o-toluidine, p-toluidine, benzidine, tetramethylbenzidene, di-anisidine, o-cresol, m-cresol, alpha-naphthol, beta-naphthol, catechol, guaiacol, pyrogallol, mixtures thereof, and mixtures of one or more of the preceding with a guaiac reagent. A preferred oxidizing-agent developing fluid is a solution of hydrogen peroxide.

In a preferred indicator wipe formed from plies of tissue paper, all of the plies are impregnated with guaiac reagent except a first outermost sheet of tissue paper adjacent to the occult-blood detection-test surface of the wipe and a second outermost sheet of tissue paper adjacent to the hand-contact surface. The outermost sheets are not impregnated with guaiac reagent to obviate any skin irritation which might be caused by contact with the guaiac reagent. In general, any single ply or all plies or any combination of plies may be impregnated with peroxidase-activity indicator reagent, if desired, provided that the indicator reagent is located sufficiently close to the detection-test surface of the wipe to permit the developing solution and hemoglobin from occult blood in specimens on the detection-test surface to interact with the indicator reagent to provide a visible indication signalling the presence of occult blood.

Although for manufacturing simplicity it is preferred that entire sheets of tissue paper included in multiple-ply indicator wipes be impregnated with guaiac reagent, it is not necessary. If desired, guaiac reagent may be dispersed on only a portion of a sheet of tissue paper. The area of a sheet of tissue paper on which guaiac reagent is dispersed, be it the entire sheet or only a portion of the sheet, may be referred to as an indicator region of the sheet.

A preferred procedure for impregnating tissue paper with guaiac reagent involves soaking the tissue paper in a solution of guaiac reagent and then allowing the solvent to evaporate, which leaves a deposit of guaiac reagent dispersed more or less uniformly on the paper. Preferred solutions for impregnating tissue paper with guaiac reagent may be prepared by dissolving guaiac reagent in a volatile organic solvent such as methanol, ethanol, isopropanol, or acetone to form a solution which is from about 0.5 percent to about 5 percent guaiac reagent by weight. A particularily preferred impregnating solution is an approximately one-percent by weight solution of guaiac reagent in ethanol. An entire roll of tissue paper may be impregnated with guaiac reagent in a single operation, after which sheets of tissue paper impregnated with guaiac reagent may be cut from the roll.

The process of the invention preferably includes a step to verify the activity of the peroxidase-activity indicator reagent and the oxidizing-agent developing fluid. To accomplish such a verification, the detection test surface of the indicator wipe preferably includes an indicator-activity verification region separate from the specimen-collection region. An indicator-activity test reagent is preferably dispersed on or located proximate to the indicator-activity verification region, and the peroxidase-activity indicator reagent is dispersed on or proximate to the verification region as well. The indicator-activity test reagent is capable of interacting with the peroxidase-activity indicator reagent and the developing fluid to provide an indication characteristic of the presence of occult blood. Thus, if a dose of hydrogen peroxide solution is sprayed on the indicator-activity verification region of such a preferred indicator wipe employing guaiac reagent as the peroxidase-activity indicator reagent, the guaiac reagent ordinarily turns from essentially colorless to blue in the verification region. Failure of the guaiac reagent in the verification region to change color is a signal that either the guaiac reagent or the developing fluid may be inactive for some reason and that any negative result of the occult-blood detection test should be suspect.

The indicator-activity test reagent preferably includes hematin, a derivative of hemoglobin with the following systematic name: [7,12-diethenyl-3,8,13,17-tetramethyl-21H,23H-porphine-2,18-dipropanoato(2-)-$N^{21},N^{22},N^{23},N^{24}$]-hydroxyiron. Hematin may be applied to the indicator-activity verification region as a basic solution in a mixture of ethanol and water. Any reagent exhibiting peroxidase-like activity; such as hemin, hemoglobin, or whole blood (either human blood or animal blood); may be used as an indicator-activity test reagent if desired, since such reagents provide a reaction with peroxidase-activity indicator reagents characteristic of occult blood.

The indicator-activity verification region is preferably substantially smaller in area than the specimen-collection region and is preferably clearly marked on the detection-test surface of the indicator wipe. The shape of the indicator-activity verification region is not critical. The verification region, for example, may be generally circular, rectangular, or of another shape. More than one indicator-activity verification region may be included if desired. A corresponding region which includes no indicator-activity test reagent may be marked on the detection-test surface as well to serve as a neutral-response region. Ink used for marking the various regions on the detection-test surface should be safe for human contact and should not give rise to a false indication of the presence of occult blood or otherwise distort the results of the test.

The indicator wipe should not include any contaminant in the specimen-collection region which would give rise to a false indication of the presence of occult blood. Commercially available grades of tissue paper such as used for toilet tissue generally do not include such contaminants.

The detection-test surface of an indicator wipe incorporating guaiac reagent is advantageously white or yellow in color to provide a visual contrast with the guaiac reagent, which turns blue on contact with occult blood. To less advantage, the surface may be colored pink. A green or blue color for the detection-test surface in this application, while possible, is generally not preferred, since a blue or green background tends to mask the color change provided by the guaiac reagent.

Preferred indicator wipes for the invention retard the seepage of developing fluid from the detection-test surface of the indicator wipe to the hand-contact surface for at least 30 seconds to give the user time to hold the wipe in his hand and observe the test results before dampness is detected on the hand-contact surface. The hand-contact surface of a preferred indicator wipe made up of nine plies of tissue paper generally remains dry to the touch indefinitely after a standard occult-blood detection-test dose of roughly 0.9 ml of a solution of hydrogen peroxide in an ethanol-water mixture is applied to the detection-test surface on the opposite side of the wipe. Although it is possible to soak such an indicator wipe through in less than 30 seconds by applying three times the standard test dose of hydrogen peroxide solution, when the standard test dose is applied, the indicator solution generally evaporates to dryness from the detection-test surface before it can penetrate to the hand-contact surface of the indicator wipe.

It is believed that the remarkable resistance to seepage from front to back in a pad of plies of tissue paper joined at their periphery is a result of the light contact the various plies make with one another in the central region of the pad. Fluid tends to flow by capillary action laterally within a sheet of tissue paper far more readily than it tends to flow from one sheet of tissue paper to the next. Moreover, the first four or five plies or so of the nine plies of tissue paper in preferred indicator wipes have sufficient fluid-holding capacity to absorb all of the developing fluid applied to the wipe in a typical occult-blood detection test.

Although in principle a moisture-impermeable polymer film could be incorporated in the indicator wipe for the invention to serve as a moisture barrier, conventional polymer films typically have too great a wet strength to be readily disposable in a toilet.

It is preferred to store indicator wipes which incorporate guaiac reagent in individual air-tight packages such as sealed foil envelopes, since guaiac reagent is subject to degradation by oxygen in the air.

BRIEF DESCRIPTION OF THE DRAWING

Preferred indicator wipes for the invention are described below with reference to the following figures.

BEST MODE FOR CARRYING OUT THE INVENTION

Figure 1:
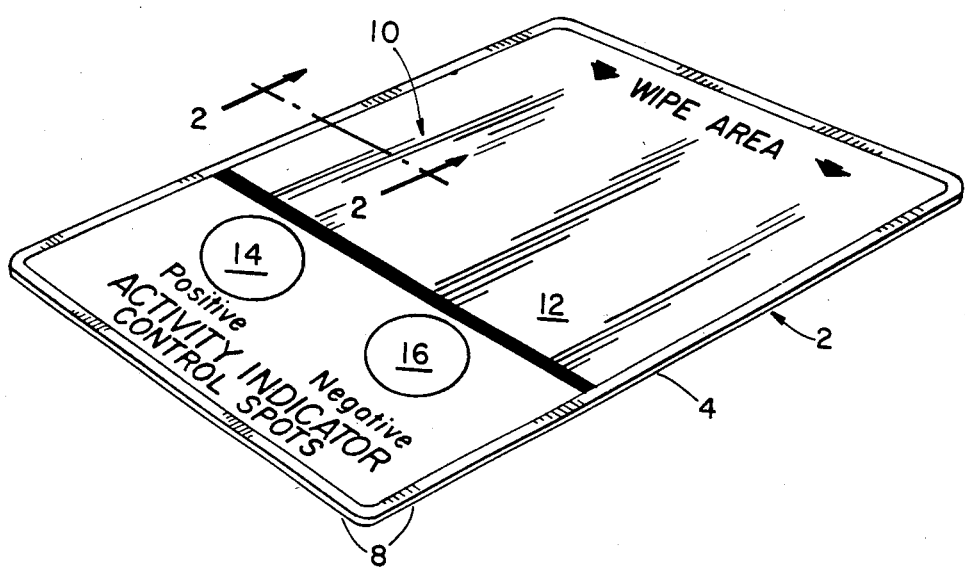
FIG. 1 is an oblique view of an occult-blood indicator wipe for the present invention.
Figure 2:
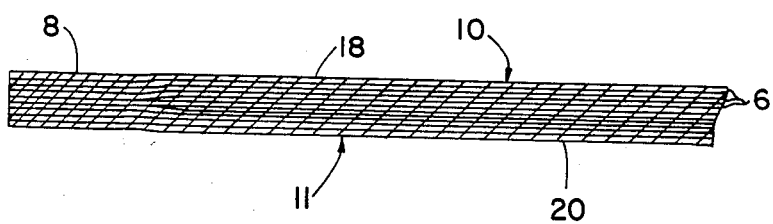
FIG. 2 is a partial cross-sectional side view of the indicator wipe of FIG. 1 taken along line 2—2.

Turning now to FIG. 1, an indicator wipe 2 includes a pad 4. As shown in FIG. 2, the pad 4 is made up of nine plies of tissue paper 6 arranged one on top of the other. The plies of tissue paper 6 are crimped together around the periphery 8 of the pad 4. A first side 10 of the pad 4 defines an occult-blood detection test surface for the indicator wipe and a second side 11 defines a hand-contact surface. Printed on the detection-test surface 10 are designations of three regions: a specimen collection region 12, a indicator-activity verification region 14 and a neutral-response region 16. The indicator-activity verification region 14 is denoted "Positive" and the neutral-response region 16 is denoted "Negative."

An outermost ply of tissue paper 18 adjacent the detection-test surface 10 of the indicator wipe 2 and an outermost ply 20 adjacent to hand-contact surface 11 are free of guaiac reagent. The remaining seven plies of tissue paper lying between the two outermost plies 18 and 20 are impregnated with guaiac reagent. An approximately one-percent by weight solution of guaiac reagent in ethanol is used to impregnate the seven intermediate plies of tissue paper. The sheets of tissue paper are impregnated with guaiac reagent by saturating them with the guaiac solution and then allowing the solvent to evaporate.

A hematin reagent is absorbed in the indicator-activity verification region 14. The hematin reagent is deposited within the indicator-activity verification region 14 by moistening the region 14 with a hematin solution, then allowing the solvent to evaporate from the moistened area to leave behind a deposit of hematin reagent. The hematin solution is prepared as follows: Water and ethanol are mixed in the proportion of about 25 percent by volume water and about 75 percent by volume ethanol. Sodium hydroxide is added to the water/ethanol mixture in an amount sufficient to form a solution of about 0.01 molar sodium hydroxide. To this basic water/ethanol solution is added a quantity of hematin sufficient to yield a solution containing about 6 mg of hematin per liter of solution.

The indicator wipe 2 and a developing solution made up of about 3 percent by weight hydrogen peroxide, about 22 percent by weight water, and about 75 percent by weight ethanol can be used as follows to test for the presence of occult blood in fecal matter. The user first obtains a sample of fecal matter by defecating. A specimen of the fecal matter is collected on the specimen-collection region 12 of the indicator wipe 2 by contacting the region 12 of the indicator wipe 2 with the fecal matter while defecating or by patting in the anal area with the region 12 of the wipe 2. The user then applies a dose of the developing solution from a spray applicator to the specimen of fecal matter on the indicator wipe. Typically, three squirts are applied, with each squirt of the applicator delivering roughly 0.18 ml of solution. In addition, single-squirt doses of developing solution are applied respectively to the indicator-activity verification region 14 and to the neutral-response region 16 of the wipe. If the guaiac reagent and the developing solution are properly active, the indicator wipe will change color in the indicator-activity verification region 14. If the indicator wipe has not been contaminated with a substance which gives a false indication of occult blood, the wipe will remain essentially colorless in the neutral response region 16. Thus, if the indicator wipe 2 either fails to turn blue in the indicator-activity verification region 14 or turns blue in the neutral response region 16, the results of the test are suspect. If the indicator wipe does not change color where it contacts the specimen of fecal matter, the specimen probably contains at most an insignificant quantity of occult blood. If, on the other hand, the indicator wipe turns blue where it contacts the specimen, the presence of occult blood is indicated and the user should consult a physician. After the test is completed the user can toss the indicator wipe into the toilet bowl and flush it away.

It is not intended to limit the present invention to the specific embodiments described above. For example, the indicator wipe may be made of flushable felt, wadding, sponge or fabric, if desired. A pad suitable for an indicator wipe for the invention may be made from sheets of creped, low-wet-strength tissue. The indicator wipe may be folded so that the indicator-activity verification region and neutral-response region generally face away from the specimen-collection region to prevent the indicator-activity verification and neutral-response regions from becoming soiled with fecal matter during the collection of specimen. After collection of the specimen, the wipe can be unfolded to permit the indicator fluid to be applied conveniently to all three regions. The indicator-activity verification region and neutral-response region may be covered with a removable, flushable paper strip or other suitable barrier to soiling if desired. The indicator wipe may be used with peroxidase-activity indicator reagents other than guaiac reagent and may be used to detect occult blood in bodily substances other than fecal matter. It is recognized that these and other changes may be made in the invention specifically described herein without departing from the scope and teachings of the instant invention and it is intended to encompass all other embodiments, alternatives, and modifications consistent with the invention.

We claim:

1. A process for collecting a specimen of a bodily substance and testing the specimen for occult blood comprising the steps of:

(a) contacting a specimen-collection region of an occult blood indicator wipe with a bodily substance to collect a specimen of the substance on the specimen-collection region of the wipe, the indicator wipe being made of a pliable pad comprising a plurality of sheets of absorbent, porous, soft material disposed one on top of another and joined together around their periphery to form a multilayer structure having sufficiently low wet strength to permit the wipe to be disposed of in a toilet, said pad including a first outermost sheet providing an occult-blood detection-test surface and a second outermost sheet providing a hand-contact surface a first region of said occult-blood detection-test surface being said specimen-collection region, and wherein a peroxidase-activity indicator reagent, in an amount sufficient to react with occult blood in the presence of an oxidizing-agent developing fluid to produce a color, is located between said first and second outermost sheets at or proximate to said specimen-collection region and said first and second outermost sheets are free of said indicator reagent, the pliable pad having a size and form to be manipulated by hand;

(b) subsequently applying an amount of an oxidizing-agent developing fluid to the specimen-collection region of the indicator wipe and observing any change in color after a predetermined period of time to determine if the specimen of bodily substance contains occult blood, providing that the peroxidase-activity indicator reagent, the oxidizing-agent developing fluid and the amount thereof, and the material of construction and number of said sheets of said pad are selected such that the wipe has a sufficiently high resistance to seepage by the oxidizing-agent developing fluid to permit the hand-contact surface of the indicator wipe to remain dry during said predetermined period to time;

(c) by subsequently placing the entire indicator wipe in a toilet bowl and flushing the toilet to dispose of the specimen of bodily substance and the indicator wipe.

2. The process according to claim 1 in which a second region of the occult-blood detection-test surface comprises an indicator-activity verification region and wherein the pliable pad is folded during the contacting of the bodily substance with the specimen-collection region so that the indicator-activity verification region faces away from the specimen-collection region.

3. The process according to claim 2 in which the plurality of sheets are made of low-wet-strength tissue paper, a plurality of the sheets are located between said first and second outermost sheets, at least one of which defines an indicator sheet, and an indicator region of each indicator sheet is impregnated with the peroxidase-activity indicator reagent.

4. The process according to claim 3 in which the sheets of tissue paper are joined together around their periphery by crimping.

5. The process according to claim 3 in which the sheets of tissue paper are joined together around their periphery by a water-degradable adhesive.

6. The process according to claim 3 in which the pad comprises nine sheets of tissue paper.

7. The process according to claim 3 in which the peroxidase-activity indicator reagent comprises a guaiac reagent and the oxidizing-agent developing solution comprises a solution of hydrogen peroxide.

8. The process according to claim 7 in which each sheet of tissue paper located between the first and second outermost sheets is an indicator sheet.

9. The process according to claim 3 in which the peroxidase-activity indicator reagent and an indicator-activity-test reagent are dispersed at or proximate to the indicator-activity verification region, the indicator-activity-test reagent being capable of interacting with the oxidizing-agent developing fluid and peroxidase-activity indicator reagent to provide a color indication when said peroxidase-activity indicator reagent and said oxidizing-agent developing fluid are sufficiently active to provide a color in the presence of occult blood, the process further comprising the step of: applying an amount of the oxidizing-agent developing fluid to the indicator-activity verification region of the wipe at about the same time as applying the oxidizing-agent developing fluid to the specimen-collection region of the wipe and observing any change in color in the indicator-activity verification region after said predetermined period to time to verify whether or not the peroxidase-activity indicator reagent and the oxidizing-agent developing fluid are sufficiently active to provide a color in the presence of occult blood.

10. The process according to claim 9 in which the indicator-activity-test reagent includes hematin.

* * * * *